(12) United States Patent
Kocher et al.

(10) Patent No.: US 11,507,924 B1
(45) Date of Patent: *Nov. 22, 2022

(54) BRAINWAVE COMPATIBILITY

(71) Applicants: Robert William Kocher, McLean, VA (US); Loran Dean Ambs, Williamsburg, VA (US)

(72) Inventors: Robert William Kocher, McLean, VA (US); Loran Dean Ambs, Williamsburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/004,900

(22) Filed: Aug. 27, 2020

(51) Int. Cl.
| | |
|---|---|
| *G06Q 10/10* | (2012.01) |
| *G06Q 10/06* | (2012.01) |
| *G06Q 30/08* | (2012.01) |
| *G16H 40/63* | (2018.01) |
| *G16H 50/70* | (2018.01) |
| *A61B 5/16* | (2006.01) |
| *A61B 5/08* | (2006.01) |
| *A61B 5/00* | (2006.01) |
| *A61B 5/369* | (2021.01) |

(52) U.S. Cl.
CPC ....... *G06Q 10/1053* (2013.01); *A61B 5/0057* (2013.01); *A61B 5/0816* (2013.01); *A61B 5/163* (2017.08); *A61B 5/167* (2013.01); *A61B 5/369* (2021.01); *A61B 5/742* (2013.01); *A61B 5/7405* (2013.01); *G06Q 10/0631* (2013.01); *G16H 40/63* (2018.01); *G16H 50/70* (2018.01)

(58) Field of Classification Search
CPC ............ G06Q 10/1053; G06Q 10/0631; A61B 5/369; A61B 5/7405; A61B 5/0057; A61B 5/163; A61B 5/167; A61B 5/0816; A61B 5/742; G16H 40/63; G16H 50/70
USPC .................. 705/1.1–912, 301, 319, 321, 320
See application file for complete search history.

(56) References Cited

U.S. PATENT DOCUMENTS

| | | | |
|---|---|---|---|
| 9,836,703 B2 * | 12/2017 | Stevens .................. | G06Q 10/00 |
| 10,470,696 B1 * | 11/2019 | McCraw ................. | A61B 5/375 |
| 2005/0177058 A1 * | 8/2005 | Sobell .................... | G16H 40/67 |
| | | | 600/545 |
| 2016/0007899 A1 * | 1/2016 | Durkee ................ | A61B 5/7267 |
| | | | 600/544 |

* cited by examiner

*Primary Examiner* — Jonathan P Ouellette

(57) ABSTRACT

A system and method for identifying individuals that compatibly contribute to high-performing teams is disclosed. Teams may range in size and complexity from a two-person team of roommates to many hundreds in a commercial product development team. Candidates for new or existing teams are identified by matching brainwave response of candidates to the brainwave signature of high-performing, compatible teams. The stimuli of stimulus datasets are rapidly presented to candidates and sensed by any of the five human senses. The signature of a team type is a set of brainwave response characteristics extracted from one or more high-performing, compatible exemplar teams presented with the stimulus dataset and is also distinctly different from other team types or the general population. Closeness of fit between a candidate's brainwave response and the signature of the exemplar team provides an indication of the likely compatible fit and contribution of a candidate to a high-performing team.

9 Claims, 13 Drawing Sheets

Sensor Location Nomenclature

FP  Frontopolar
F   Frontal
T   Temporal
P   Parietal
O   Occipital

Odd-numbered electrodes are on the left
Even-numbered electrodes on the right
Midline electrodes are designated as "z."

| Peak | Latency | Evoking Stimuli | Interpretation |
|---|---|---|---|
| P1 | 50 ms (auditory) 100 ms (visual) | None specific | reflects level of arousal; suppression of unattended information |
| N1 | 100 ms (auditory) 100 ms - 165 ms (visual) | None specific | Selective filtering, basic stimulus characteristics, initial selection for later pattern recognition |
| P2 | 150-275 ms (auditory) 200 ms (visual) | None specific | Selective attention, Stimulus change, feature detection, short-term memory |
| | 200 ms (auditory) | None specific | Detects changes in stimuli that are attended to |
| N2 | 156–189 ms aka N170 (visual) | human faces, complex objects, words | Facial and/or expert object recognition |
| | 100-300 ms Auditory & Visual | Go/NoGo | inhibition |
| MMN | 100-250 ms (auditory) | physically different infrequent stimuli among other more frequent stimuli | early pre-attentive sensory memory |
| P3 | 300 ms | Attention to stimuli, low probability of targets | memory updating, stimulus discrimination and responses preparation |
| | 300 ms | Novel stimuli, not requiring attention | involuntary attention, inhibition |
| N400 | 200–500 ms, peaks: 475 ms (auditory) 525 ms (visual) | Semantically deviant words | Semantic meaning |
| | 300-500 ms aka FN400 | memory tasks | familiarity of stimuli |
| | 350-1200 ms (non-specific) | Recognition memory tasks (old/new decisions) | recollection |
| P600 | 600ms (non-specific) | Syntactic and morphosyntactic violations | syntactic reanalysis and repair |

FIG. 13

BRAINWAVE COMPATIBILITY

CROSS-REFERENCE TO RELATED APPLICATIONS

This application incorporates herein, by reference, in their entirety, U.S. Pat. No. 10,238,310 filed on Dec. 20, 2016 and patent application Ser. No. 15/530,894 filed on Mar. 20, 2017.

BACKGROUND

Field of the Invention

The field of this invention relates to electronic brain monitoring techniques.

Description of the Related Art

Considerable effort is expended by individuals and groups of individuals in order to shape teaming relationships of individuals that share common interests and objectives in interpersonal relationships (e.g., dating, marriage, social club and/or collaborate in performance of tasks [e.g., work crews]). In its simplest form, a team is composed of two or more individuals in a social setting (e.g., roommates, dating, marriage) and as large as a multi-disciplinary team to design, develop and market products for worldwide distribution. Great effort is expended to optimize team composition in order to ensure that team members have attributes and characteristics (e.g., interest, personality, skills, experience, abilities, aptitudes, financial resources, ethics and attitudes) leading to a compatible relationship between team members that function well together.

Persons or organizations striving to replicate high-performing, compatible teams need the means to identify the characteristics of high-performing and compatible teams and characteristics of the compatible persons, enabling high-performance of the teams and compatibility among the team members. Contributions of team members span the range of easily quantified to highly subjective. Contributions of individual members of high-performing teams may share certain common characteristics and may add other complimentary or contrasting characteristics, to differing degrees, depending upon the objectives of the team. A team optimized for the function of roommates would have significant similarities and differences than a team optimized for marriage. Identifying the characteristics needed for team success and the individuals best suited to provide the necessary characteristics, in the right measure, has proven over time to be a very difficult undertaking.

Conventional structured approaches to assessing the interests and personality traits of candidate team members have relied upon questionnaires and standardized tests, such as the Myers-Briggs Type Indicator and similar instruments. Administration of these instruments requires a substantial time commitment for the candidate to read or listen to questions and record responses on paper or electronic media. Such questionnaires and personality inventories can be compromised by intentional or unintentional self-reporting biases of the candidate being tested. Pencil-and-paper test instruments allow the candidate time to consider the question and shape a response suited to how the candidate wishes to be perceived, rather than providing the strictly objective response. Some prior art techniques employed observations and interpretation of non-verbal (passive) responses to questions such as body language, gestures and facial expressions. Tests based on written or spoken stimuli can be limited in their ability to probe the full spectrum of the psyche of the candidate. Conventional tests can also limit the responses to stimuli related to very simplistic binary answers or multiple-choice answers recorded by pencil, paper, or electronic means. Interpretation of test results requires subjective assessments of skilled personnel. Consequently, conventional testing to predict the suitability of persons to perform particular functions in a team has often proven unreliable due to the subjective nature of the assessment. Thus, conventional personality type indicators may not have the necessary fidelity needed to elucidate subtle but important characteristics which are essential for high-performance with compatibility in a team environment.

DESCRIPTION OF THE SEVERAL VIEWS OF THE DRAWINGS

FIG. 13 Is a chart showing various scientific designations for brainwave responses to stimuli, according to an exemplary embodiment of the invention.

DRAWING REFERENCE NUMERALS

Figure 1:
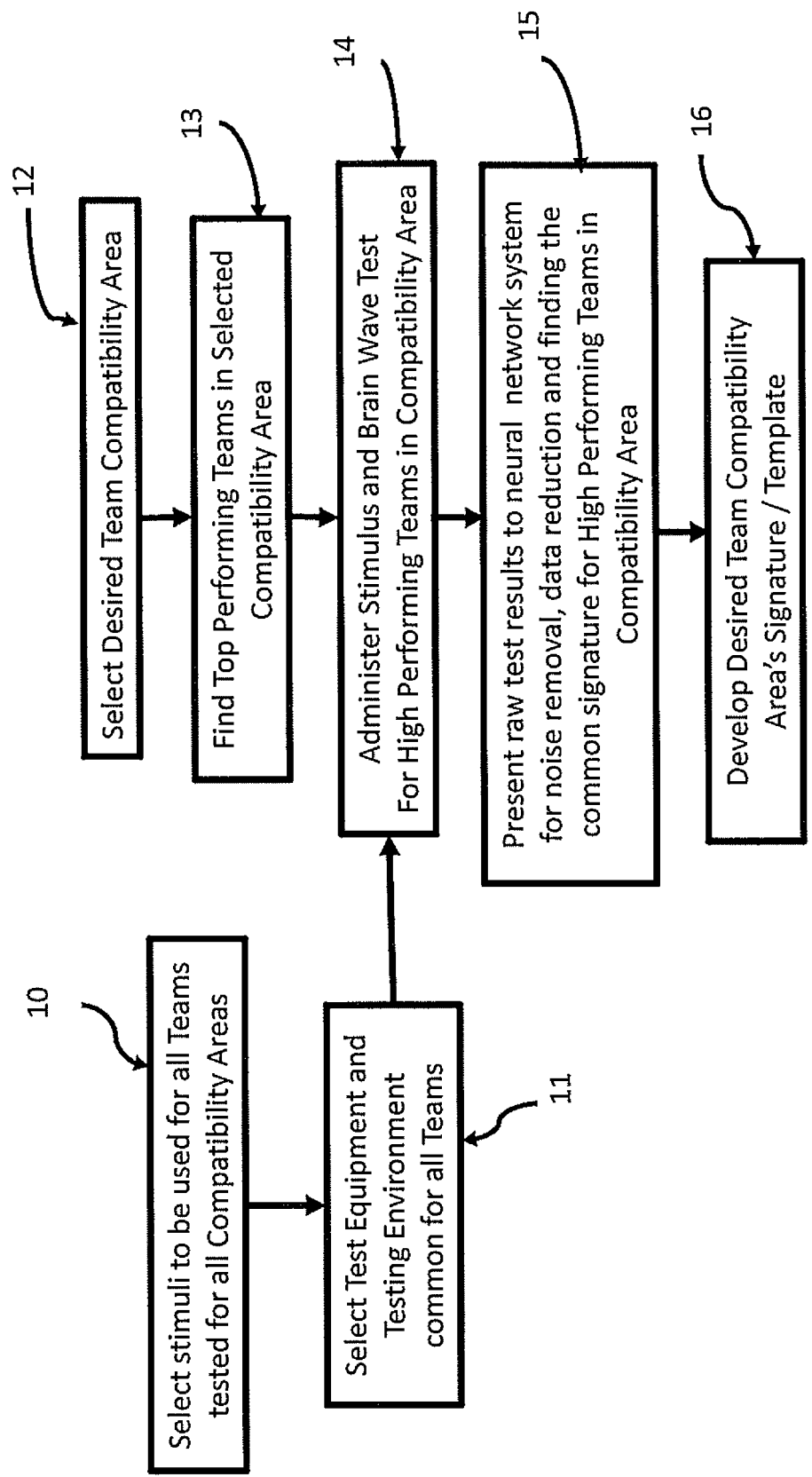
FIG. 1 illustrates a block diagram of the steps used to select the stimuli needed to develop a common test, in conjunction with selecting one desired team arrangement set, and team members of high-functioning of teams, and the process utilizing neural networks to develop a signature/template.

10 Selection of Stimuli
11 Selection of Testing Equipment and Testing Environment
12 Selection of the Team Compatibility Area
13 Finding High-performing Teams in the selected Compatibility Area
14 Administering Stimulus and Brainwave Test
15 Presenting raw test data to a computer Neural Network system, in order to search for commonality and reduce noise.
16 Developing the Desired Team Compatibility signature/template
20 Group of Teams
21 Individual Teams
22 Compatibility Areas
23 Individual Compatibility Areas
30 Teams, Groups, Organizations
31 Example Group—roommates
32 Example Group—tank crew
33 Example Team—sports team
34 Example Team—sports group
35 Example Organization—sports organization
36 Example Organization—business organization
40 Example of two person teams and couples conducting testing, and compatibility scoring matching
41 Example of person 1 results of testing
43 Example of person 2 results of testing
44 Example of merging and matching test results of person 1 and person 2
45 Example of specific high scoring team compatibility: boy/girlfriend
46 Example of specific high scoring team compatibility: friends
47 Example of specific high scoring team compatibility: co-workers
48 Example of specific high scoring team compatibility: husband/wife
49 Example of compatibility area scores
50 Example of three or more person teams, groups, or organizations conducting testing, and compatibility scoring matching
51 Example of matching response comparing three or more persons
52 Example of different responses from at least one person in response to the same stimuli
53 Example of similarities of responses from all persons
54 Example of testing response from third or more persons being tested
55 Example of high scoring team compatibility scores from various team, groups or organizations
56 Example of specific high scoring team, group or organization compatibility: management group
57 Example of specific high scoring team, group or organization compatibility: sports team
58 Example of specific high scoring team, group or organization compatibility: business group
59 Example of specific high scoring team, group or organization compatibility: friends group
101 Identification of high-performing teams of a particular Team-of-Interest
102 Identification of common physiological characteristics
103 Identification of stimuli for testing
104 Identification of physical measures of response to stimuli
105 Test stimuli on high-performing individuals of the same skill set.
106 Determine confidence in signature match or no match
107 Administer stimuli set to candidates of Team-of-Interest
108 Correlate candidate responses
109 Refine stimuli set
110 Does candidate response match?
111 Add to Team-of-Interest
112 Reject
201 Team-of-Interest stimuli
202 Team-of Interest signature
203 Stimuli set database
204 Team-of-Interest Signature Database
205 Administer Stimuli Set to Team-of-Interest Candidates
206 Correlate Candidate Response with Team-of-Interest Response
207 Report Correlations
301 EEG data processing computer
302 EEG sensors
302a EEG sensor cable harness
303 Interviewee
305 Interviewee support structure
308 Interviewee input device
312 Graphical display device
314 Control computer
315 Data and synchronization cable
316 System support structure
317 Stimuli database
318 GOI signature database
401 Represents a positive response to stimuli
402 Represents a negative response to stimuli
403 Represents person 1 and person 2 no-match to same stimuli
404 Represents person 1 and person 2 match to same stimuli
501 EEG data processing computer
502 EEG sensor
503 Interviewee
504 EKG Sensor
505 Respiration band
506 Chair
507 Shaker
508 Interviewee input device
509 EKG data processing computer
510 Audio output device
511 RF Transmitter/Receiver
512 Graphical display device
513 Camera
514 Control computer
515 Data synchronization
516 System support structure
517 Stimuli database
518 Team-of-Interest signature database
700 Computing Device
710 Data bus
720 Display
730 User input
740 Fixed storage
750 Removable media
760 I/O controller
770 Memory
780 Processor
790 Network Interface
800 Network
810 Client 820 Client
830 Remote platform
840 Server
850 Database
860 Data store
870 Data store

DETAILED DESCRIPTION OF THE EXEMPLARY EMBODIMENTS

According to an exemplary embodiment of the invention, "Team Compatibility by Brainwave Analysis" or "Brain Compatibility" described is a method and system to identify individuals that possess common, complimentary, contrasting and compatible traits, aptitude and interests necessary to form a high-functioning team which performs in business, athletics, academics, military, social settings, etc. In a preferred exemplary embodiment, Brain Compatibility is accomplished in a three-step process: 1) identify the brainwave signature for a high-performing team which is indicative of the collective personality traits, cognitive traits and interests of the team, 2) identify the brainwave signature of constituent team members, and 3) identify the most compatible combination of candidate individuals that collectively match the brainwave signature of the high-performing team. These steps enable the judicious selection of team members to produce a highly functional team with strong compatibility among the team members. Characteristics of the team members may include, but are not limited to, personality traits, interests, preferences, aptitude, knowledge, ethics, and beliefs. By optimizing team compatibility (technical and interpersonal), the time on the Tuckman Model of Team Development (i.e., forming, storming, norming and performing) is dramatically shortened.

Indicators of these characteristics are obtained by measuring psychophysiologic responses to a substantially standardized test of large numbers of stimuli engineered to elicit responses. Psycho physiologic responses may represent any involuntary response to external stimuli. In the preferred implementation of this technique, the measured psychophysiologic response is obtained by one or more electroencephalogram (EEG) sensors, but may also include other indicators of psychophysiologic response, such as pupillography, blood pressure, pulse, respiration, and skin conductivity. Brainwaves detected by EEG are measures of the electrical activity of the brain in response to external stimuli presented to a test subject.

Stimuli may be sensed by any of the five human senses; sight, hearing, smell, taste and touch. Visual, audible and tactile stimuli modalities are most compatible with electronic presentation devices. Visual stimuli may include still and video imagery, words, numbers and phrases. Audible stimuli may include spoken words, phrases, tones, music or other natural or man-made sounds. Tactile stimuli may include touch points, movement, single or multiple repetition rates or duration, as well as broadband stimuli, such as an impulse. Stimuli may be presented in one or more modalities simultaneously, at rates of about 10× per second. Consequently, a test subject can be exposed to a very large number of stimuli in a relatively short period of time without introducing self-reporting biases, which are prevalent in pencil-and-paper instruments used to assess interest, aptitude, personality and/or cognition. Standardized stimuli tests can include hundreds to thousands of images, sounds and/or tactile probes which generally produce a brainwave response in a test subject.

Machine learning techniques employing deep neural networks and/or other techniques driven by artificial intelligence may analyze the test results. In an implementation of this disclosure, brainwave responses from test subjects exposed to a stimuli data set designed for the functional team-of-interest may be compared, using deep neural network techniques, to responses from other test subjects in order to identify a combined signature or other response common to high-performing, compatible teams. Examples of high-functioning and low-functioning teams may be used to train the machine learning algorithm on the distinctive characteristic of high-functioning teams.

Response signatures or commonalities may be stored as a template for that team function. In a similar way, templates for various other functional teams may be determined based on their response to the same standardized test stimuli. These templates may be compiled into a set of high-performing team templates. New test subjects may then be tested using the standardized test stimuli. The results of the new test subjects may be analyzed for correlation with the set of high-performing team templates. Subjects with a strong correlation to a specific team template may be determined to have a significant probability of performing well in the specialized area of a the specific team associated with that specific template.

Machine Learning/Artificial Intelligence (ML/AI) techniques may be used to quantify the degree of similarity or compatibility score between a particular high-functioning team type and combinations of candidate team members, to populate new high-performing teams of the same type for the purpose of identifying minimum differences in the team. Compatibility scores may also be computed using rule-based algorithms, factor analysis, and pair-wise comparisons, such as the Jaccard Similarity Index.

Data analysis by ML/AI or other means may be used to identify deficiencies in poor-functioning teams, for corrective action. Weighting factors on team and team member characteristics may be made with or without the aid of automated analysis, in order to influence the degree of performance or compatibility of the team or interactions between team members. The ability to modify the weighting factors on teams or team member characteristics, allows team organizers to experiment with trade-offs of team performance and/or member compatibility.

Additional benefits of Brain Compatibility, in accordance with an exemplary embodiment of the invention, may be that a person turned away from the initial team-of-interest could be guided to other teams where he/she is perhaps better suited to contribute compatibly.

Implementations of this disclosure may solve the long-standing problem of identifying candidates that are compatibly suited to perform in a particular functional team. This can be accomplished by matching the psychophysiologic response of a candidate exposed to a set of sensible stimuli with the psychophysiologic response characteristic of a population of high-performing teams of interest exposed to the same set of sensible stimuli. In one exemplary embodiment, the psychophysiologic response may be observed by sensing a variety of brainwaves resulting from graphical stimuli. The system and process are capable of also presenting stimuli using any of the five human senses and observing psychophysiologic responses such as brainwaves, pupillary response, eye movement, heart rate, heart rate variability, respiration, electrodermal activity, and other responses, as are well known in the art.

Technical literature is replete with examples of distinctive characteristics of high-functioning teams formed for particular outcomes. Implementations of this disclosure may facilitate the assessment of suitability for compatible contributions to a particular team. Application of this disclosure spans the range from an individual seeking a match for a two-person social relationship to many thousands of people trying to identify which type of functional team arrangement they might be best suited (e.g., military occupational specialty). Implementations of this disclosure can also be used for persons to explore teaming arrangements they are best suited for, so that they can pursue appropriate training to prepare them for entry or transition in the work force.

One problem with any new data stream can be knowing how to make sense of it, understand the information it contains, and exploit the information for some purpose. Brainwaves can be characterized as time-varying voltages that are caused by neural activity and measured with an array of sensors in contact or proximal to the scalp. In an implementation of the disclosure, pattern matching may be employed in order to identify individuals whose brain responses to certain stimuli are similar to that of individuals who are very successful and compatible in particular teaming arrangements. As an example, if a young person's brainwave signature response to stimuli is similar to the two-man crew of a Co-pilot/Gunner of an Apache helicopter gunship, then it may be expected that the young person might also, with training, become an excellent Co-pilot/Gunner of an Apache helicopter gunship crew.

Brainwaves may include weak signals having a significant quantity of noise. Implementations of the disclosure may take an exploratory approach, that can identify correlations in brainwave data and extrapolate patterns based on machine learning techniques employing deep neural networks and/or other artificial intelligence techniques.

Implementations of this disclosure of machine learning techniques may be based on statistical classification or computational neural nets (inspired by, but not to be confused with, biological neural nets, such as the human brain). These machine learning techniques can enable the use of many different inputs without regard to a user's ignorance as to which inputs are important or even having a concept of what the inputs represent. In the case of a neural network such as a multi-layer perceptron, a large number of inputs can be used including those used to characterize the stimuli, the brainwaves of the person being measured, and temporal delays used to model the brain's latency. As the network operates, weights on processing nodes may be adjusted nonlinearly using an algorithmic feedback known as backpropagation. Over time and many empirical examples in a labeled training data set, the input nodes that are unimportant to pattern classification can have their weights adjusted towards zero while those that are significant can have weights that increase. In this way, the neural network can "learn" (through weight adjustment) different patterns, such as the brainwave patterns of exemplar humans who represent the best, most successful, and most compatible individuals in particular team arrangements (or as described above, teams and functional teams). These different patterns can be expressed as a vector of the outputs of the neural network; but they can be quite recognizable and characteristic of the various exemplar teams and team members. Thus, after training, the neural network can now classify new persons as having brainwave patterns that respond most similarly to one of the exemplars (or team template, as discussed above). One obvious use for such a neural network may be to identify teaming arrangements to suggest to young people. If a young person's brainwave response to certain stimuli is similar to an exemplar team member of a particular team, then it may be likely that the young person's brain is predisposed to enable success in that team environment.

A statistical classifier can be equivalent to a computational neural net for pattern recognition. Thus, implementations of this disclosure may employ techniques in addition to neural networks, such as similar machine learning methods, or other artificial intelligence driven techniques.

The inputs to the machine learning techniques discussed herein can include the brainwaves of a test subject who is responding to certain stimuli. Brainwaves can vary by frequency and amplitude, as well as the rates of change in frequency and amplitude, based on changes in stimuli. Furthermore, in addition to brainwaves, other types of psychophysiologic responses may be analyzed, including but not limited to pupillary response, eye movement, heart rate, heart rate variability, respiration, and electrodermal activity. All of these factors can be inputs to the machine learning system because they are potentially correlated to brainwave response. For example, brainwave frequency can be correlated to state-of-mind, computational load on the brain, and certain personality characteristics, such as the degree of extroversion/introversion.

A computing device may execute various procedures for determining a brainwave signature or template for a team group of high-performing individuals, according to implementations of this invention. For example, FIG. 1 shows an example procedure, where at 10, stimuli may be selected to be used as standardized stimuli for all team members for all team compatibility areas. This test may consist of a significant number of stimuli such as hundreds or thousands of photos of various subjects, numbers, letters, objects, faces, abstract art, geometrical shapes or 3-D presentations. An average human brain can process 12 stimuli or pictures a second. At this speed, it is hard to recognize photos consciously. However, the human brain functions subconsciously at a faster rate and generates measurable brain response activity to various stimuli. With the brain processing 100 to 500+ photos a minute, thousands of diverse photos can be used. Photos may be selected that have a bold subject and solicit a strong response.

In implementations of this disclosure, once the standardized stimuli selection has been made, the common test equipment and testing environment of 11 can be selected. Since a test goal may be to measure variations between individuals, the test setup may be configured to reduce as many variables as possible.

As discussed above, one benefit of implementations of this disclosure may be to determine if unknown persons are mentally wired like members of a high-performing team. The first step may be to select the sought-after teaming arrangement at 12 and then identify the high-performing individuals in this area at 13. For example, a first set of subjects may be a set of high-performing individuals with respect to a sought teaming arrangement; and the first selection criteria may be the sought-after teaming arrangement determined at 12. In some implementations, a second set of subjects may be a randomly sampled set of persons selected from the general population or a related baseline set of test subjects. The second selection criteria may be that the second set of subjects are randomly selected or otherwise selected in a manner that results in a suitable baseline of personnel.

Once test subjects are identified, they may be presented with the standard stimuli at 14. For example, a sensory presentation device, such as a video screen or projection system may be communicatively connected to a computing device. The sensory presentation device may present the first sequence of stimuli from the standardized stimuli to the set of individuals forming a high-performing team. In some implementations, the sensory presentation device may also present the first sequence of stimuli to the second set of subjects.

During or after presentation of the standardized stimuli, one or more electrodes operatively connected to each of the high-performing individuals and in communication with the computing device, may detect a first set of one or more voltage fluctuation sequences from each of the individuals of the high-performing team. In some implementations, during or after presentation of the standardized stimuli, one or more electrodes operatively connected to each of the second set of subjects and in communication with the computing device, may detect a second set of one or more voltage fluctuation sequences from each of the second set of subjects.

Once the individuals of the high-performing team complete the test, their raw test data can be submitted at 15 to a computing device implementing machine learning techniques that can identify commonality in brainwave data among the subjects of the teaming arrangement of interest. For example, a neural network executing on the first computing device may determine a pattern of voltage fluctuations that are characteristic of the first set of voltage fluctuations. This characteristic pattern may be stored as a template and associated with the high-performing individuals, at 16. In some implementations, the neural network may determine a pattern of voltage fluctuations that are characteristic of the first set of voltage fluctuation sequences and not characteristic of the second set of voltage fluctuation sequences. This determined pattern that is not characteristic of the second set of voltage fluctuation sequences, and may be selected as the characteristic pattern for the individuals of the high-performing team and stored as a template.

In some implementations, machine learning techniques such as neural networks may execute on computing devices such as one or more remote servers executing in a cloud computing environment in communication with a local computing device and/or sensory presentation device, as discussed herein.

In some implementations, the procedure discussed with respect to FIG. 1 may include providing, by the first computing device, a recommendation for a selection of subjects from among a third set of subjects based on the pattern of voltage fluctuations. For example, a third set of subjects may be presented with the standardized stimuli and their brainwave responses to the stimuli may be compared to the stored template associated with the high-performing individuals. The brainwave responses of a subset of subjects within the third set of subjects may be determined to exhibit a correlation with an individual's template that exceeds a threshold value. In response to this determination, this subset of the third set of subjects may be recommended for consideration for joining the high-performing team-of-interest. In some implementations, recommendations as discussed herein may be provided to other systems such as employee recruitment systems or components of human enterprise resources information systems, and serve as a basis for further functionality of those systems. In some implementations, recommendations may be provided to an interface for a user of a computing device.

Figure 2:
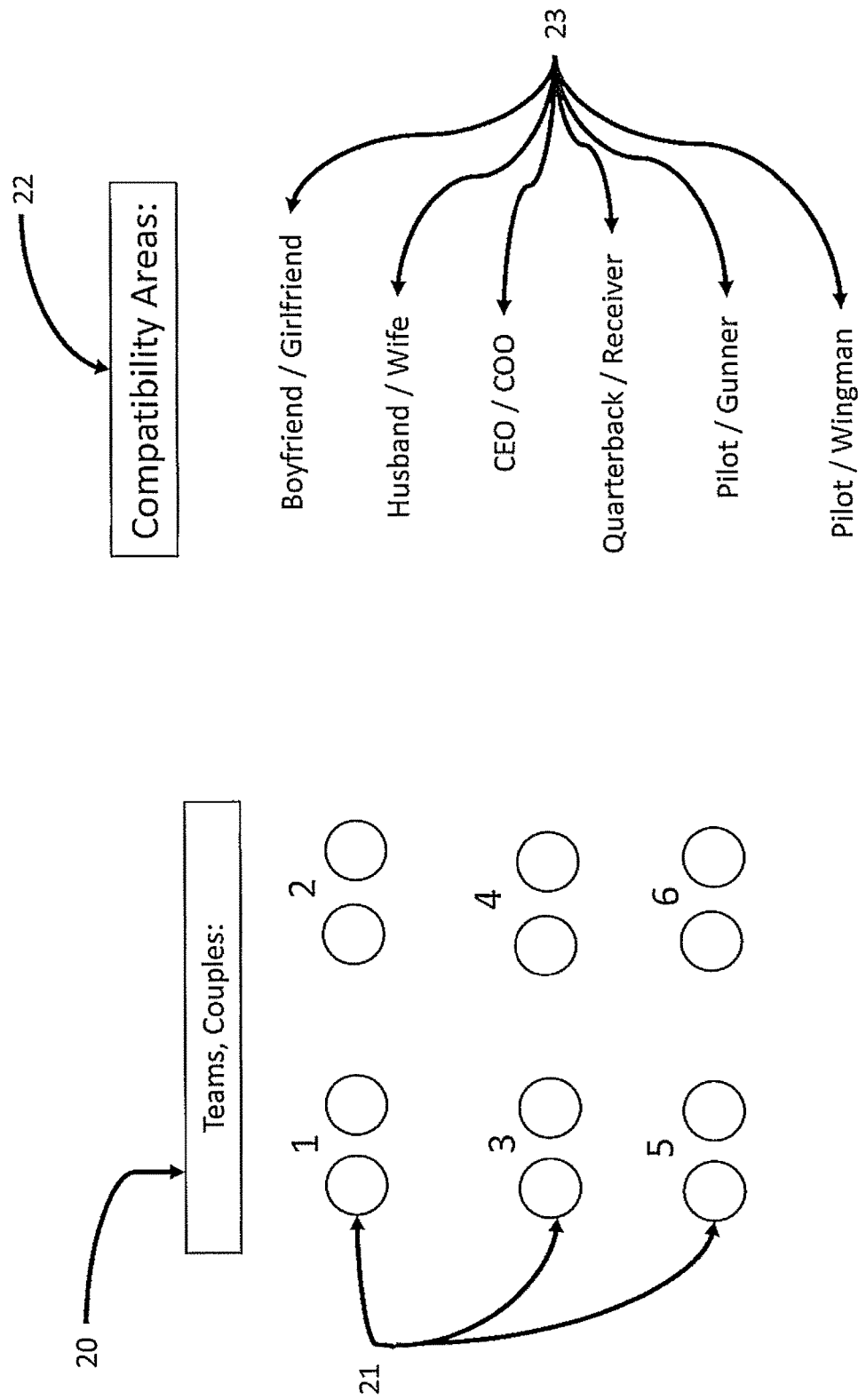
FIG. 2 illustrates some examples of two-person teams and potentially matching high-performing, compatible team functions.

FIG. 2 illustrates teaming arrangements of two person teams or couples 20, 21 on the left-hand side of the figure, which may be matched to certain team functions 23 on the righthand side of the figure. For example, team 1 of the set of teams 20 may be a couple that would like to know their compatibility based on looking at the same stimuli and registering various brainwave results. These brainwave results collected on each person would be combined to result in a combined score for each stimuli item. The combined common and different stimuli responses would establish a team signature which would then be further correlated to successful teams in the desired performance area. A specific example would be to examine the compatibility of a boyfriend/girlfriend couple and determine their compatibility in marriage. The system would first submit brainwave testing on many successful married couples until a compatibility signature is developed. Failed marriage couples would also be submitted to brainwave testing and a preliminary signature would be developed. The successful marriage signature would be compared to the unsuccessful marriage signature in order to further refine each signature by removing common stimuli responses in both groups with the same stimuli. The resulting signatures would be less similar to each group resulting in a more defined signature. Once strong signatures are established with successful marriages and failed marriages, the boyfriend/girlfriend couple would compare their signature to the successful and failed married groups and determine their correlation to which group. If they have a strong correlation to successfully married couples based on their independent brainwave tests with the same stimuli, one could conclude that they have compatibility with respect to how they view and respond to the same stimuli.

Figure 3:
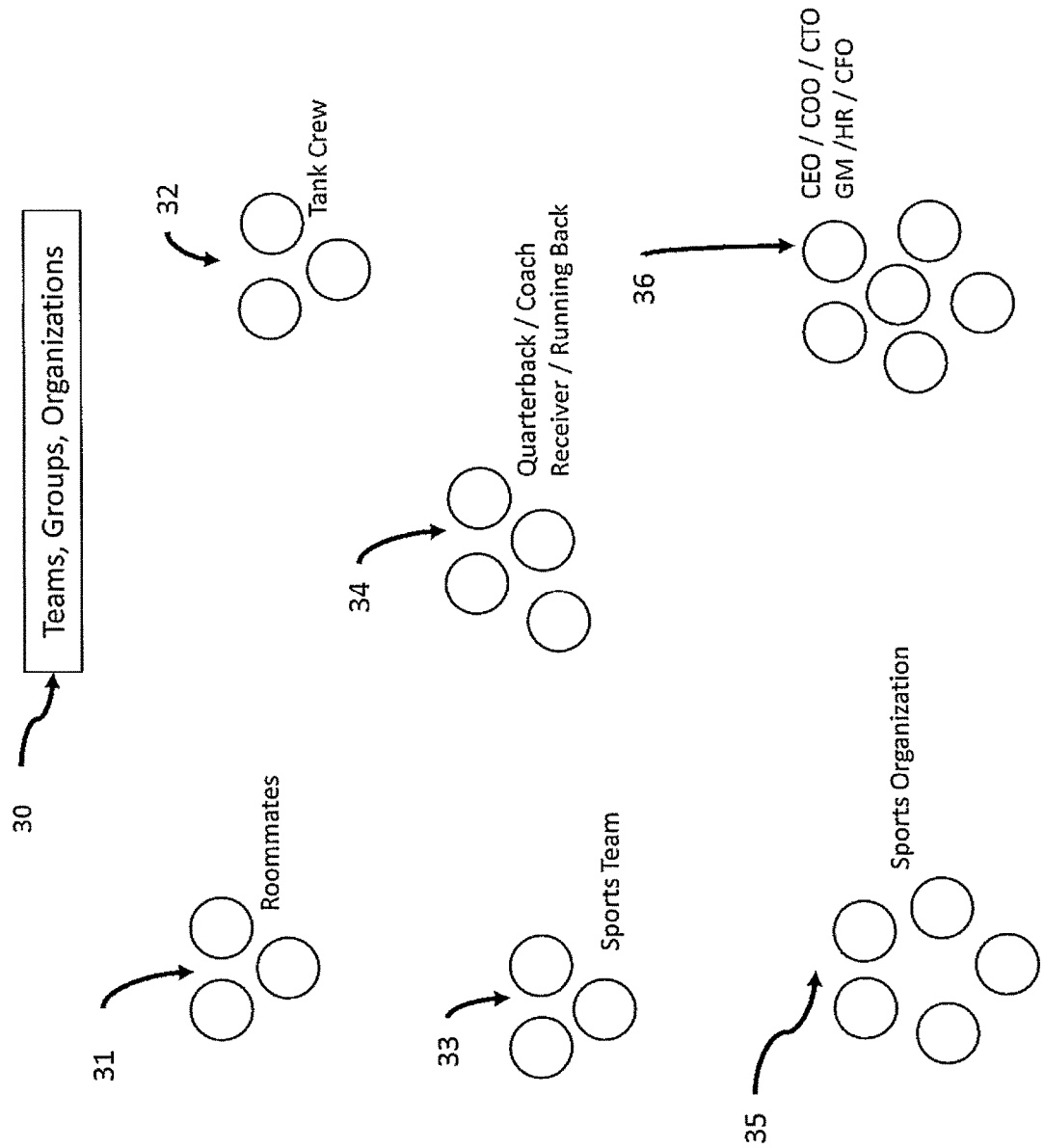
FIG. 3 illustrates some examples of multi-person teams and potentially matching high-performing, compatible team functions.

FIG. 3 illustrates multi-person teams (N>2) and potential team functions. This approach is similar to the discussion in FIG. 2, above, with the exception that each team/couple consists of more than two persons. Teams, Groups, and Organizations 30 can vary the spectrum of multi-party social relationships, such as roommates 31, to sports 33, 34, 35, and on to professional organizations, such as a key member of a business 36 or small teams, such as military fighting tank crews 32.

Figure 4:
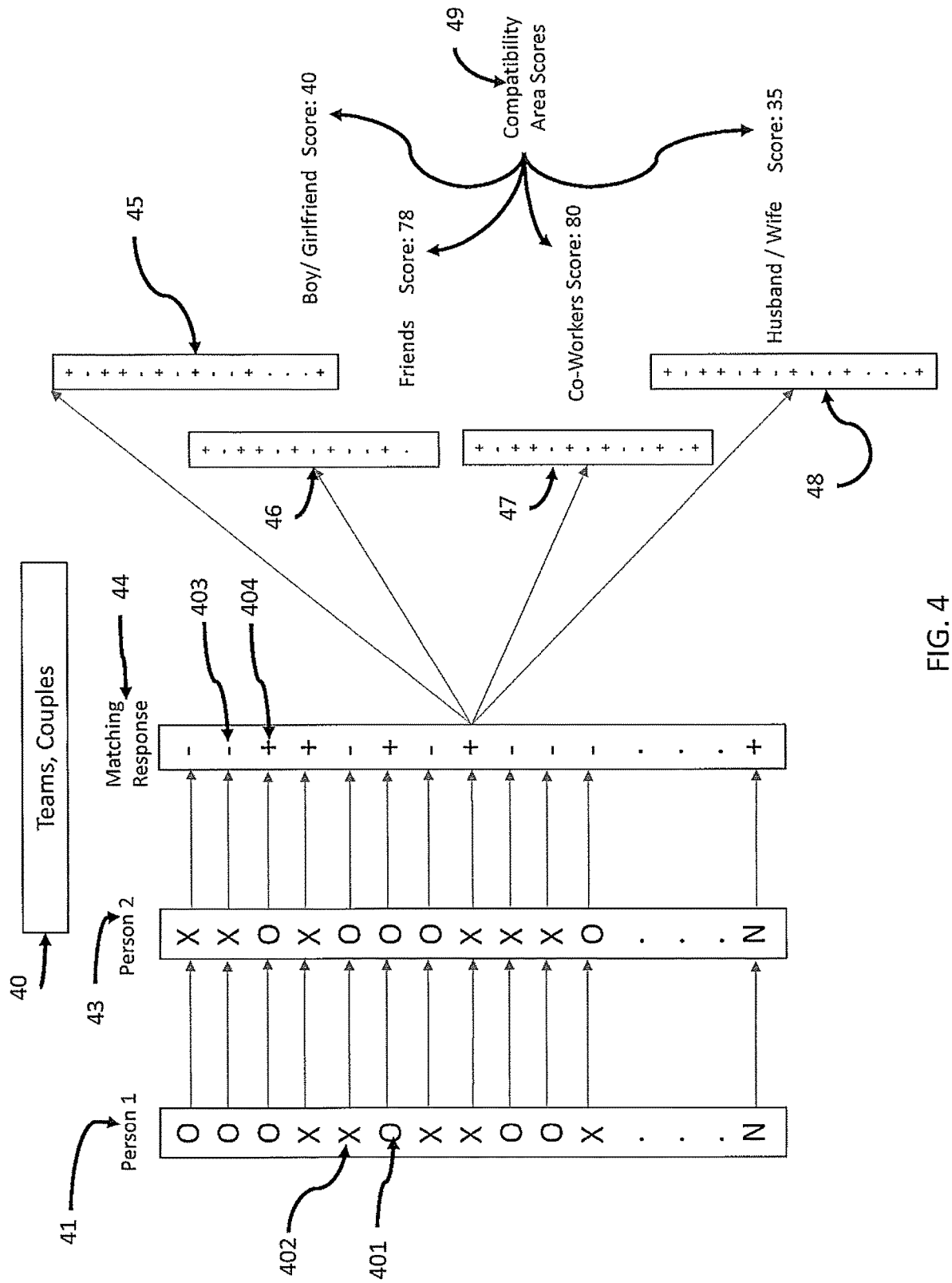
FIG. 4 illustrates responses for two persons to each of N stimuli, comparison of the individual responses, and a compatibility score calculated for each of several team relationships.

FIG. 4 illustrates the response of two individuals presented with multiple stimuli. The response of each individual 401, 402, is tabulated in Columns 41 and Column 43. Indications of the of common responses are tabulated in Col 44. Comparison of Column 44 and templates derived for particular team functions provides an individual matching 404 or difference 403 for each stimulus. As discussed above, successful and unsuccessful teams in specific area 45, 46, 47 and 48 would develop a signature profile to determine through a matching algorithm the comparative compatibility score by looking at numerous stimuli, such as 2000 images in less than 5 minutes. Based on specific stimuli that is part of the existing desired team's signature, a compatibility score 49 can be calculated and compared to the persons in question. For purposes of illustration, matching response 44 of FIG. 4 is expressed as a simple binary indication of similarity or dissimilarity of response by each of persons in columns 41 and 43. Matching response 44 could contain much more information than a simple binary indication of similarity. For instance, the degree of similarity or dissimilarity may be noted. The functional roles of the persons forming the team-of-interest may be an important factor in the compatibility area scores 49. Signatures of a high-performing team-of-interest may indicate that compatibility among team members is achieved by appropriate differences in personality, drive and attention to detail. For instance, many high-performing and compatible teams will have appropriate representation of complimentary personalities adept at task planning, organization, execution, communication and reporting independent of their functional roles. In other teaming arrangements, high-performance and compatibility of team members is promoted by specific differences associated with specific roles of the teammates. For example; a team focused on product development, will exhibit differences in responses to stimuli indicative of specialized knowledge, personality traits and cognitive characteristics for complimentary roles and responsibilities of persons performing program management, finance, engineering and sales.

Figure 5:
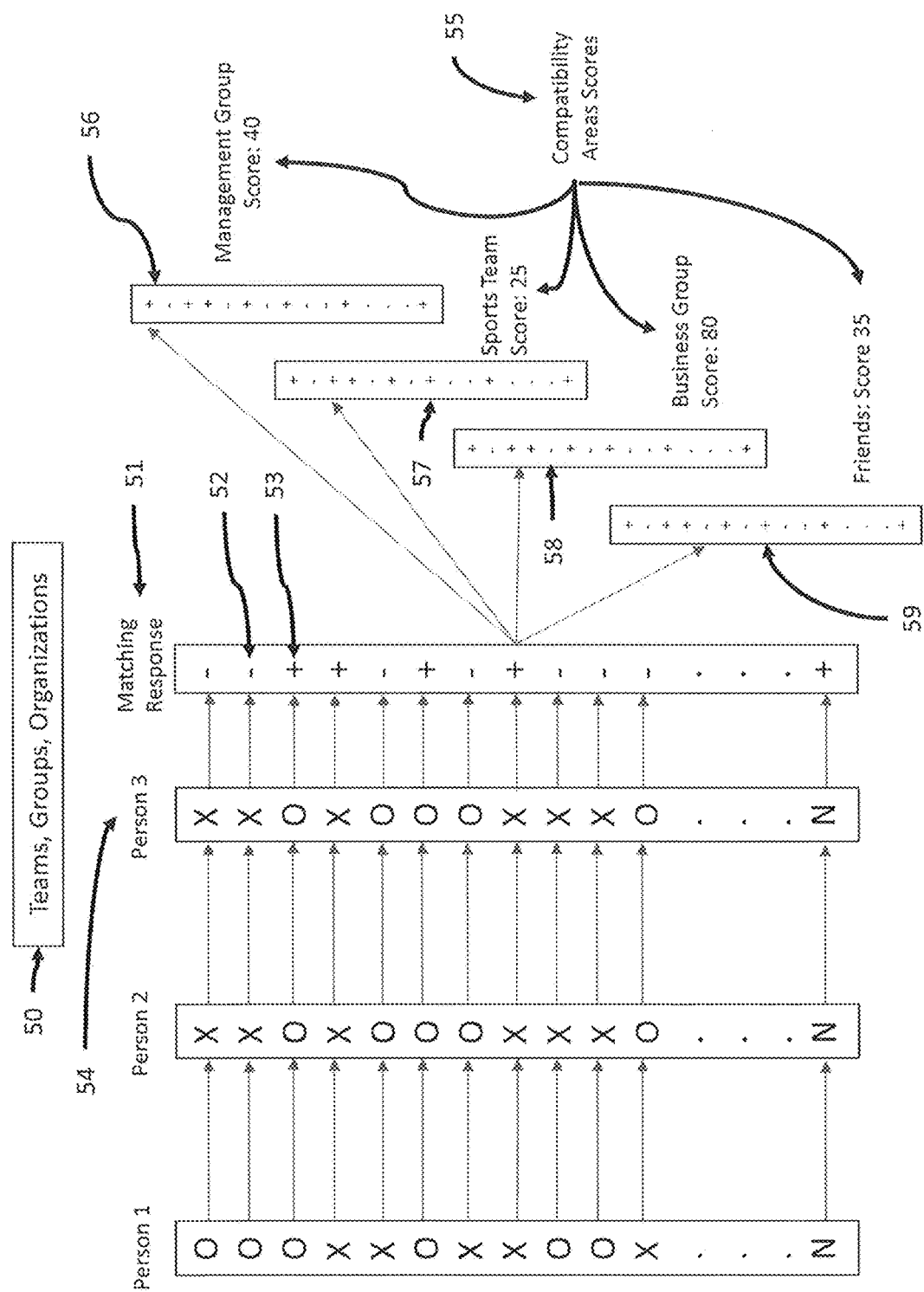
FIG. 5 illustrates responses for three persons to each of N stimuli, comparison of the individual responses, and a compatibility score calculated for each of several team relationships.

FIG. 5 illustrates a process similar to the process illustrated in FIG. 4, but for teams, groups or organizations 50 which are composed of more than two persons. The stimuli test results 54 of Person 3 or more, are combined with Person 1 and Person 2 to result in a matching response 51. Similarity of responses 53 and dissimilar responses 52 make up the team's signature. Again, this signature is compared to the successful teams, groups, and organizations 56, 57, 58 and 59, and through a signature matching algorithm, will develop a team compatibility score 55.

Figure 6:
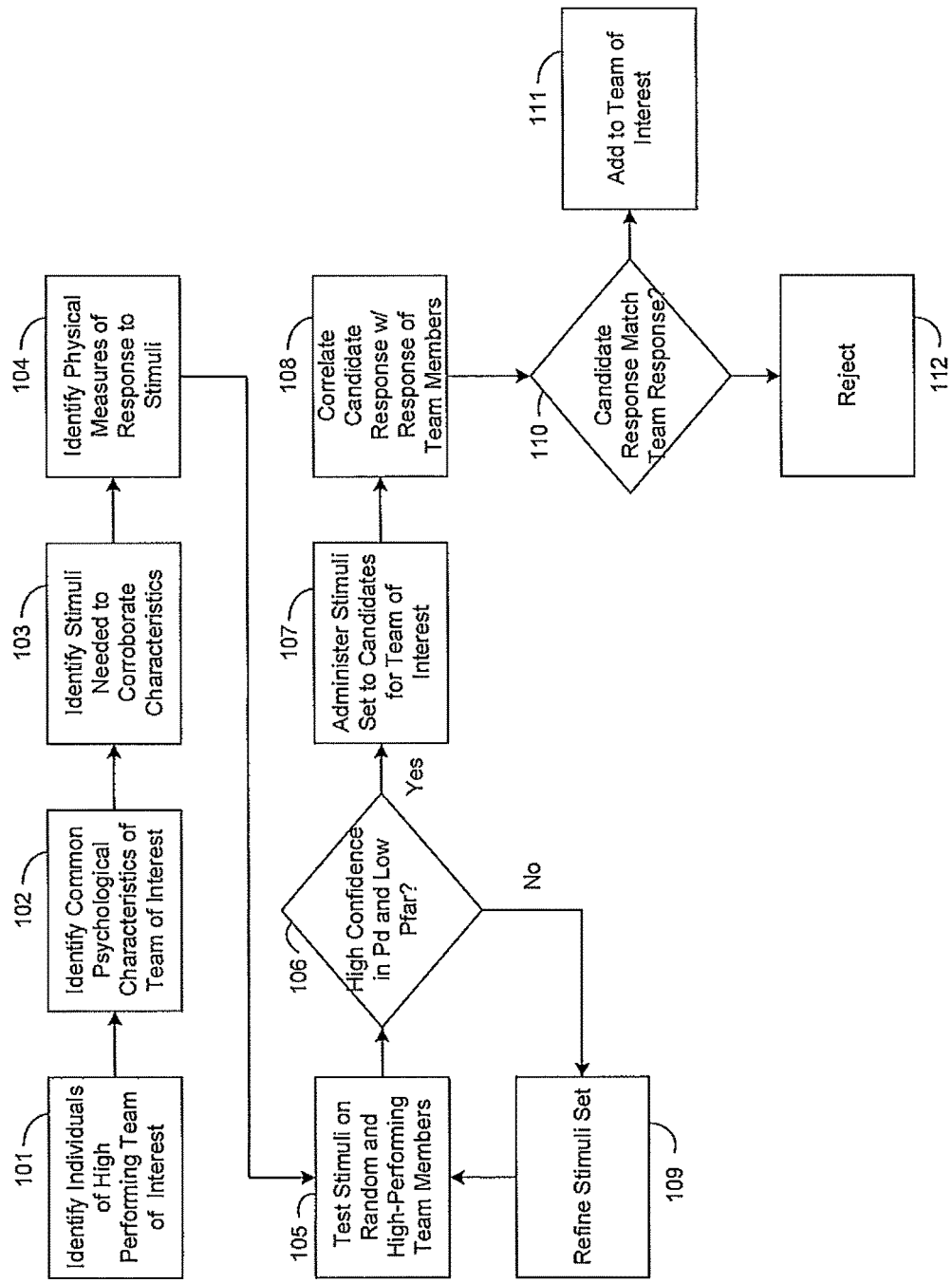
FIG. 6 illustrates a block diagram of the steps taken to assess the compatibility of multiple candidates for a single team function, according to an implementation of an exemplary embodiment of the invention.

FIG. 6 illustrates a flow diagram describing the processes of establishing the characteristic signature of a high-functioning and compatible tea; observing stimuli response of candidate persons to populate another high-functioning and compatible team which performs the same or similar duties. In this process, one or more high-function teams are identified as being exemplary (101) and their characteristics common characteristics are identified at (102). At 103, stimuli are identified to elicit meaningful responses from the exemplary team or teams. At 104, the appropriate measures of stimuli response are identified. At 105, the stimuli data set is presented to individuals of the exemplary team(s) and random individuals. Results of the brainwave responses to the test subjects of 105 are compared to establish the degree to which persons from the high-functioning teams can be reliably identified from the combined populations.

If the brainwave response of the individuals from the high-functioning exemplar team(s) members is distinctly different from that of the general population (e.g., their signature) with high probability of detection (Pd) and low probability of false alarm rate (Pfar), then the set of stimuli may be validated to be reliably predictive, and can be administered to candidates. If not, then the stimuli set may be modified in step 109 and re-evaluated in steps 105 and 106 until the stimuli set is deemed sufficiently predictive.

Once the stimuli set is validated as predictive with high Pd and low Pfar, it can be administered to candidates for membership in new instantiations of the exemplar teams in step 107. The psychophysiologic response of candidates to the stimuli data set may be correlated to that of the members of the exemplar team(s) response to the same stimuli set. The strength of the correlation predicts how well the candidate matches the response of the exemplar team members, and thus the probability that the candidate will also be a strong performer in a team arrangement of interest; step 110. If the strength of match exceeds a threshold value, the candidate may be deemed to be a fit in the team arrangement of interest, step 111. If not, the candidate may be deemed unlikely to fit in the team-of-interest.

Figure 7:
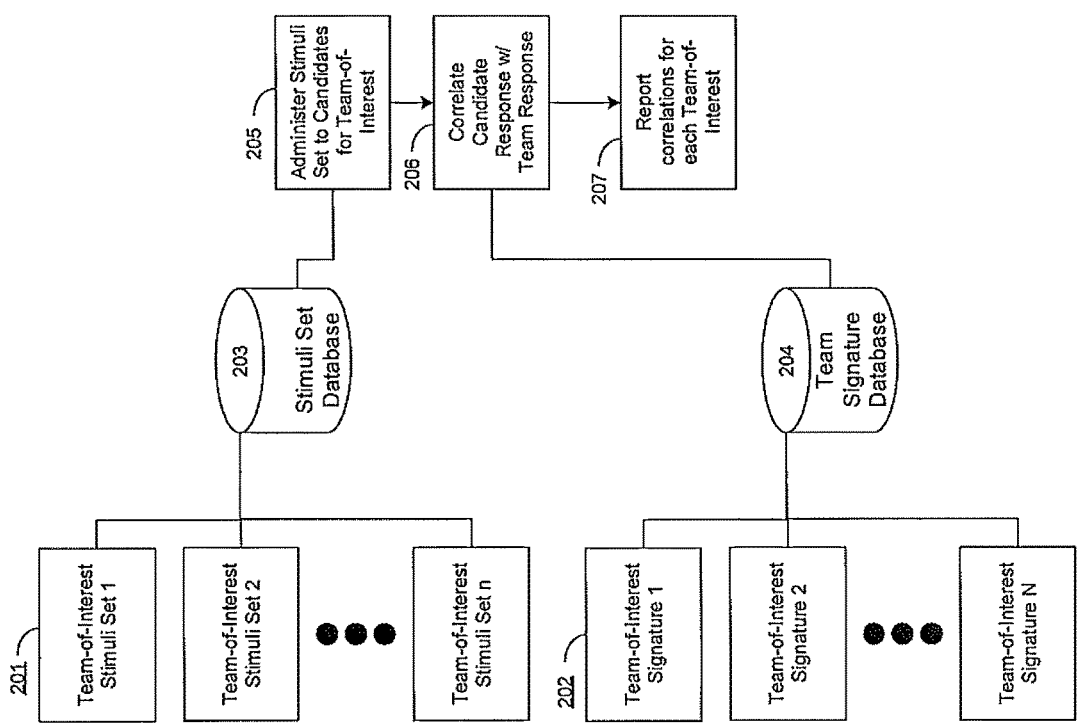
FIG. 7 illustrates a block diagram of the steps taken to assess the compatibility of multiple candidates for multiple team functions, according to an implementation of an exemplary embodiment of the invention.

FIG. 7 illustrates an extension of the process and system described in FIG. 6. The process in FIG. 4 evaluates the degree of fitness of candidates to multiple teams. The steps of FIG. 6 may be implemented for multiple tasks or functions so that a library of diagnostic stimuli sets 201 is populated in database 203. The distinctive signatures for multiple teams of interest 202 may populate a signature database, 204. The library of stimuli data sets may be administered to candidates for the corresponding teams of interest in step 205. The response of the candidate to the stimuli may be correlated to those of the signature's characteristic of the teams of interest in step 206. Closeness of fit of the candidate to the teams of interest represented may be tabulated in a report 207.

Figure 8:
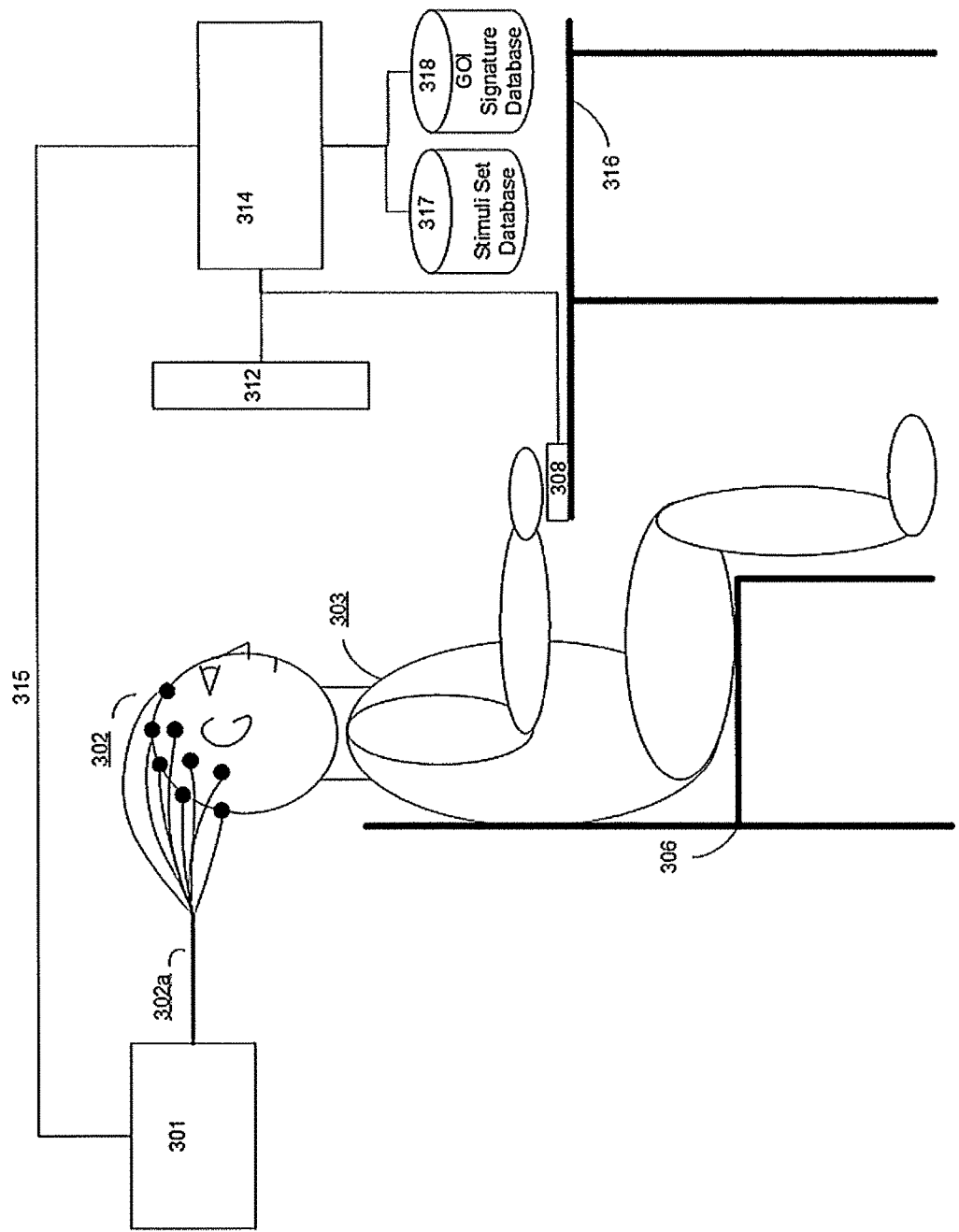
FIG. 8 illustrates instrumentation employed in an essential embodiment of the system, working on brainwave psychophysiologic response to external stimuli, according to an essential exemplary embodiment of the invention.

FIG. 8 illustrates an embodiment of this invention. An interviewee 303 is seated before a graphical display device, 312. In this particular embodiment, stimuli 317 may be graphical in nature and are displayed on the graphical display device, 312. Stimuli elements, for instance still images, may be displayed at fixed intervals for fixed durations of time in the method of rapid serial visual presentation (RSVP), which is well known in the art. Graphical presentation of stimuli by RSVP typically displays images at a rate of 5 to 10 images per second.

Figure 9:
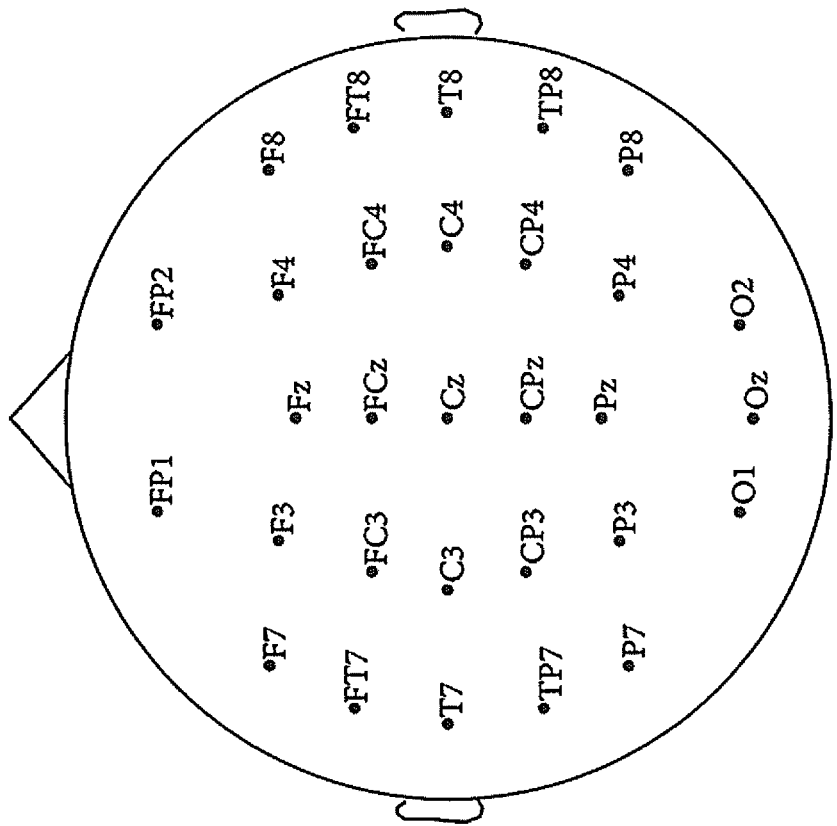
FIG. 9 illustrates brainwave sensor locations for 30 sensors, according to an exemplary embodiment of the invention.

One or more sensors 302 may be arranged on the test subject's head in locations according to locations illustrated in FIG. 9 for a 30-channel system, in an exemplary embodiment. The number and location of channels may differ upon the stimulus presented to the interviewee 303. The sensors and data collection and processing collectively facilitate electroencephalography (EEG). Sensor locations may be selected to obtain strong signals for specific brainwaves resulting from the RSVP stimuli. Brainwave signals may have characteristic shape, polarity and latency which is well established in the art. FIG. 13 represents a Table which describes well known brainwave features, their polarity, latency, evoking stimuli and interpretation. Brainwave response to stimuli is rich in information beyond the features described in FIG. 13. Algorithms based on Machine Learning and Artificial Intelligence are able to extract subtle features from brainwave data beyond the conventional features of FIG. 13.

Communication means 315 may provide a channel for data to be transferred between EEG data processing computer 301 and control computer 314. Channel 315 may also provide the timing data needed for EEG data processing computer to know when stimuli is presented to the interviewee 303 so that brainwave latency can be computed. This channel may be a wired or wireless connection, and may use any data format or protocol known in the art.

Interviewee input device 308 may be used to keep the interviewee 303 attentive to the graphical display device 312 while RSVP of the stimulus data is in progress. For instance, the interviewee may be asked to indicate the display of a particular image by pressing on a keyboard or activating a switch. Input device 308 may also be used to measure interviewee response time, motion inhibition response and similar psychophysiologic responses.

Figure 10:
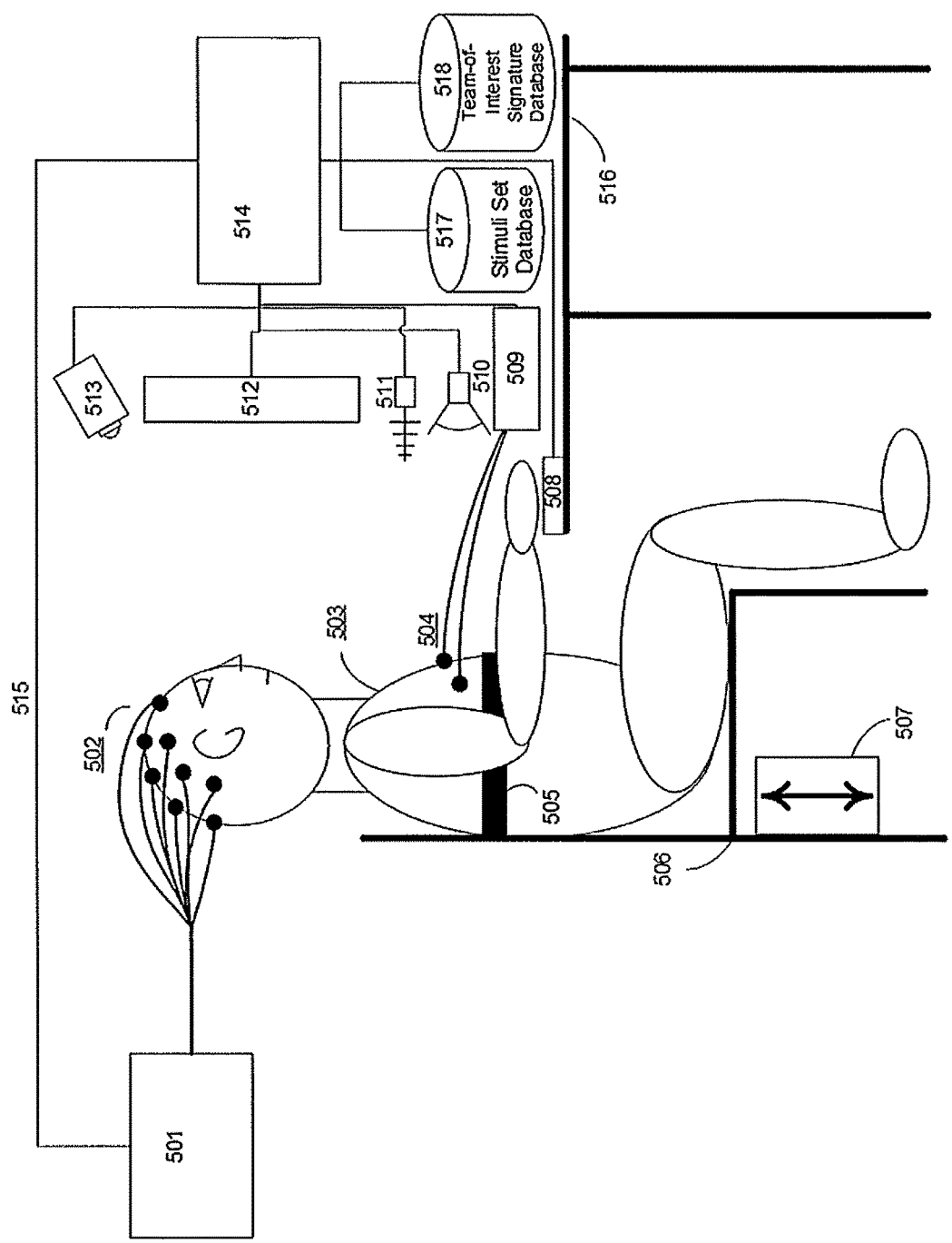
FIG. 10 illustrates instrumentation employed to produce multiple sensor inputs and multiple sensors used to observe psychophysiologic response to external stimuli, according to an exemplary embodiment of the invention.

FIG. 10 illustrates a system in which stimuli may be delivered to multiple human senses and multiple sensor types are employed in order to observe psychophysiologic response to the multi-modal stimulation. Stimulus generating components may include the audio output device 510 and shaker 507 which is capable of imparting signals affecting the sense of touch of the interviewee. For clarity in the figure stimulus generators affecting the senses of taste and smell, are not shown, but could form a part of this system as would be understood by one skilled in the art.

Sensors of the system described in FIG. 10 may include the EEG system components 501 and 502; electrocardiogram (EKG) sensors 504 and EKG data processing computer 509; respiration band 505, RF transmitter/receiver 511, which can be used to measure heart rate, heart rate variability and respiration using RF Doppler vibrometry, electrodermal activity; and a camera 513 to observe pupillary response, eye movement, and muscle tension. In alternative exemplary embodiments, different subsets of these sensors may be used. The system configured in this way can produce one or more sensible stimuli and monitor one or more psychophysiologic responses to the stimuli.

FIG. 13 is a Table listing several brainwave features in response to various stimuli. For instance, the P-300 brainwave has proven very effective at indicating a test subject's level of recognition of sounds, words, numbers or images. Appropriate stimuli can be generated and presented to the test subject and responses of the test subject are recorded. Because the purpose of this system is to establish characteristic patterns of response to stimuli, the exact stimuli need not be limited to elucidating personality traits alone.

The response to stimuli may result in a set of measured values with fixed and known ranges. One example is measured voltage from a brainwave as measured by an electrode placed at a particular location on the scalp, as illustrated in FIG. 9. To classify a response, a set of these measured values in addition to a digital description of the particular stimuli can be input into a classifier, such as a neural net (e.g., a multi-layer perceptron using back-propagation during training) or another equivalent classifier algorithm. The output may be a vector of values that characterize a team or members of a team that perform well in a particular teaming area. This vector of outputs may be a refined version of the raw values measured and thus a good, general method of measuring the response to stimuli. The classifier described in this paragraph is a common component in all exemplary embodiments.

Description of a Preferred Embodiment; RSVP/EEG for Single Team-of-Interest

In a preferred exemplary embodiment of the invention, the process of FIG. 6 and the instrumentation of FIG. 7 may be employed to assess the fit of candidates for a single team-of-interest.

Operation of the Preferred Exemplary Embodiment

In an exemplary embodiment of the invention, the process of FIG. 6 may be employed to establish the characteristic signature response of a subset of a particular team-of-interest that is assessed to represent high-performing individuals of that team-of-interest. Through iteration of testing and refinement, a set of graphical stimuli may be validated to distinguish between known members of the group of interest and known non-members of the team-of-interest with a high probability of detection and low false alarm rate. The validated stimuli set can then be administered to individuals by RSVP and resulting psychophysiologic response observed by EEG, as illustrated in FIG. 8, in order to determine if the individuals fit the characteristic of the team-of-interest, or not. The elements of the stimuli set may be reordered within a stimulus dataset presentation or mixed amongst the various stimuli datasets presented.

Embodiment 2; Single Non-RSVP Input, EEG Sensors and Single Team-of-Interest In an alternative exemplary embodiment of the invention, the process of FIG. 6 and the instrumentation of FIG. 8 may be employed to assess the fit of candidates for a single team-of-interest using stimuli sets evoking psychophysiologic response by inputs affecting senses other than the sense of vision.

Operation of the Exemplary Embodiment 2

In this exemplary embodiment of the invention, the process of FIG. 6 may be employed to establish the characteristic signature response of a subset of a particular team-of-interest that is assessed to be high-performing individuals of that team-of-interest. Through iteration of testing and refinement, a set of graphical stimuli may be validated to distinguish between members of the team-of-interest and non-members of the team-of-interest with a high probability of detection and low false alarm rate. The validated stimuli set may be composed of inputs to a single human sense other than by sight such as hearing, touch, taste or smell and is administered to individuals by RSXP where X can be Hearing (H), Touch (T), Smell (S) or perception of flavor or gustatory system (G). The resulting psychophysiologic response may be observed by EEG as illustrated in FIG. 8 to determine if the individuals fit the characteristic of the team-of-interest, or not. The elements of the stimuli set may be reordered within a stimuli set presentation or mixed amongst the various stimuli sets presented.

Exemplary Embodiment 3; RSVP/EEG for Multiple Teams of Interest

An alternative embodiment of the invention may be configured to assess the fit of one or more candidates to more than one team-of-interest by RSVP and EEG.

Operation of Exemplary Embodiment 3

In this exemplary embodiment of the invention, the process of FIG. 6 may be employed to establish the characteristic signature response of high-performing individuals for each of more than one team-of-interest. For each of more than one team-of-interest, a set of graphical stimuli may be validated to distinguish between known members of each team-of-interest and known non-members of each team-of-interest, with a high probability of detection and low false alarm rate. The multiple stimuli sets associated with each team-of-interest can then be administered to individuals by RSVP and resulting psychophysiologic response observed by EEG as illustrated in FIG. 8 to determine how well they fit each of the teams of interest. The elements of the stimuli set may be reordered within a stimuli set presentation or mixed amongst the various stimuli sets presented.

Embodiment 4; RSXP/EEG for Multiple Teams of Interest

An alternative exemplary embodiment of the invention may be configured to assess the fit of one or more candidates to more than one team-of-interest by RSXP and EEG.

Operation of Exemplary Embodiment 4

In this exemplary embodiment of the invention, the process of FIG. 6 may be employed to establish the characteristic signature response of high-performing individuals for each of more than one team-of-interest. For each of more than one team-of-interest, a set of graphical stimuli may be validated to distinguish between known members of each team-of-interest and known non-members of each team-of-interest with a high probability of detection and low false alarm rate. The multiple stimuli sets associated with each team-of-interest can then be administered to individuals by RSXP and resulting psychophysiologic response observed by EEG, as illustrated in FIG. 8, to determine how well they fit each of the teams of interest. The elements of the stimuli set may be reordered within a stimulus set presentation or mixed amongst the various stimuli sets presented.

Exemplary Embodiment 5; RSVP, No EEG Sensors, Single Team-of-Interest

An alternative embodiment of the invention, a stimulus set to characterize a single team-of-interest may employ RSVP and observations of psychophysiologic responses other than brainwaves.

Operation of Embodiment 5

In this exemplary embodiment of the invention, the process of FIG. 6 may be employed to establish the characteristic signature response of a subset of a particular team-of-interest that is assessed to be high-performing individuals of a particular team-of-interest. Through iteration of testing and refinement, a set of graphical stimuli may be validated to distinguish between known members of the team-of-interest and known non-members of the team-of-interest with a high probability of detection and low false alarm rate. The validated stimuli set can then be administered to individuals by RSVP. The resulting psychophysiologic response may be observed by instruments other than EEG sensors. Candidate sensors may include one or more cameras sensitive to the visible and non-visible components of the spectrum (e.g., infrared) to monitor pupillary response, eye movement, vasodilation, muscle tension, etc.; electrocardiogram for heart rate and heart rate variability; respiration band for respiration rate and abnormalities; RF Doppler vibrometry to observe heart rate, heart rate variability, respiration and muscle movements; skin resistivity measures electrodermal activity. Laser Doppler vibrometry performs the same function as RF Doppler Vibrometry. There are many other sensor modes for observing psychophysiologic responses that are well known in the field of polygraphy, that will also be employed measurements commonly used in this exemplary embodiment.

Exemplary Embodiment 6; RSVP, No EEG Sensors, Multiple Teams of Interest

An alternative exemplary embodiment of the invention provides a stimulus set to characterize multiple teams of interest, and employs RSVP and observations of psychophysiologic responses, other than brainwaves.

Exemplary Embodiment 7; RSXP, No EEG Sensors, Single Team-of-Interest

An alternative exemplary embodiment of the invention provides a stimulus set to characterize a single team-of-interest, and employs RSXP and observations of psychophysiologic responses, other than brainwaves.

Exemplary Embodiment 8; RSXP, No EEG Sensors, Multiple Teams of Interest

An alternative embodiment of the invention provides a stimulus set to characterize multiple teams of interest, and employs RSXP and observations of psychophysiologic responses, other than brainwaves.

Exemplary Embodiment 9; RSVP and RSXP, EEG Sensors, Single Team-of-Interest

An alternative exemplary embodiment of the invention provides a stimulus set to characterize a single team-of-interest, which may employ a combination of RSVP and RSXP in conjunction with brainwave observations accomplished by EEG instrumentation.

Exemplary Embodiment 10; RSVP and RSXP, EEG Sensors, Multiple Teams of Interest

An alternative embodiment of the invention provides a stimulus set to characterize multiple teams of interest, which may employ a combination of RSVP and RSXP in conjunction with brainwave observations accomplished by EEG instrumentation.

Exemplary Embodiment 11; RSVP and RSXP, EEG and Non-EEG Sensors, Single Team-of-Interest An alternative exemplary embodiment of the invention provides a stimulus set to characterize a single team-of-interest, which employs a combination of RSVP and RSXP in conjunction with EEG and non-EEG observations.

Exemplary Embodiment 12; RSVP and RSXP, EEG and Non-EEG Sensors, Multiple Teams of Interest An alternative exemplary embodiment of the invention provides a stimulus set to characterize multiple teams of interest, which employs a combination of RSVP and RSXP in conjunction with EEG and non-EEG observations.

Exemplary Embodiment 13; Multiple Candidates Evaluated Concurrently for Each of the Exemplary Embodiments Above Exemplary Embodiment 14; an Example or Embodiment for Using the Brain Compatibility Invention, May be for Military Service Selection Before a new recruit makes a decision on branch of service or which occupational specialty the recruit wishes to pursue (Infantry, Armor, Logistics, mechanic, etc.), the soldier could be told that he is mentally wired like high performers of one or more team arrangements. The soldier would then have significantly important information to assist him or her and the military in selection of training that yields optimized technical and interpersonal compatibility for the soldier.

Exemplary Embodiment 15; Dynamic Selection of Stimuli Sets

Candidates for teams can be evaluated by dynamically selected stimuli sets which are automatically selected by the system based on how well a candidate matches teams of interest at high levels of abstraction. For instance, if a candidate's responses match better with a team-of-interest for general engineering compared to other vocational types, the system may select stimuli sets from a lower tier of engineering disciplines that provide more specificity in engineering such as mechanical, electrical or software. Levels of specificity for any particular functional category may not be limited.

Exemplary Embodiment 16; Unlimited Personality Type Indicators

Over time, as the Brain Compatibilty invention builds, an inventory of brainwave templates for numerous teams of interest, these templates can be assembled to allow a team candidate to identify which team-of-interest he/she would best fit. This embodiment could assemble thousands of teams of interest to provide very specific matching.

Exemplary Embodiment 17; Synthetic Teams of Interest

This Exemplary embodiment will allow taking the stimuli results from team candidates and group the candidates in teams which have not previously been characterized. An example is testing numerous candidate personnel who, after testing, do not fit in any previously characterized teams. Based on stimuli test results, these subjects may be grouped/paired by stimuli to form a new team-of-interest.

Additional Alternative Exemplary Embodiments

The Brainwave Compatibility technique can be employed to identify the best match for the technical and interpersonal contributions of a team member who is departing a team-of-interest. Selection of the replacement team member will be designed to improve team performance and/or compatibility among the other team members.

The Brainwave Compatibility method and system may be used to improve the compatibility of a performing team-of-interest and the recipient of the products of the team-of-interest. For instance, a team optimized to provide a particular service may be selected for interpersonal compatibility with a particular customer of that service. Examples may include pairing a sales force to a buying agent, assigning teachers to classes, and adopted children to adopting parents.

The Brain Compatibility method and system can be used to replicate a team-of-interest by identifying the best match among candidates to replicate each team member of an exemplar team. The Brain Compatibility technique may also be used to replicate a high-functioning team by finding the minimum number of candidates to satisfy the team characteristics, without regard to team member roles of the exemplar team.

Figure 11:
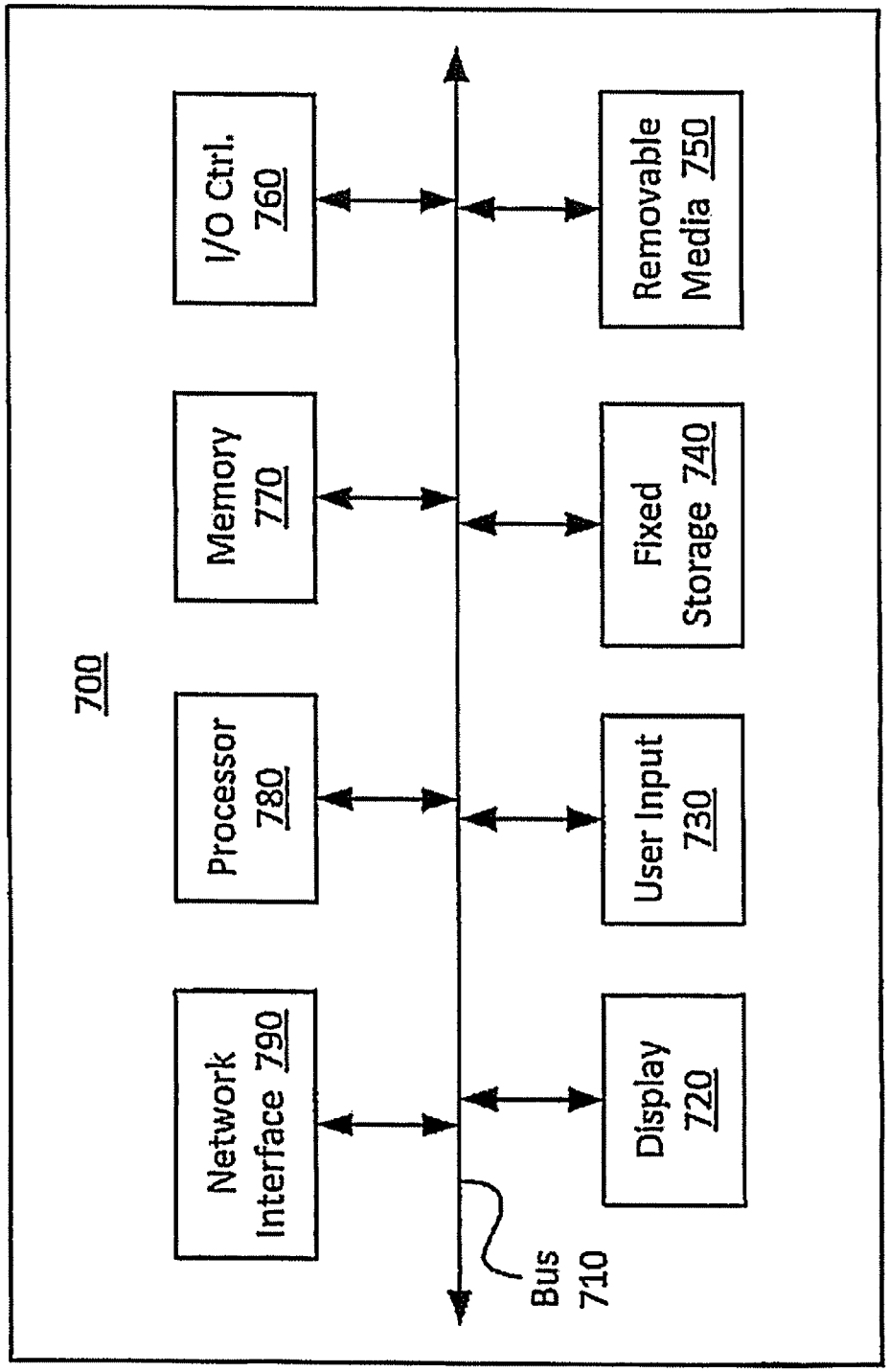
FIG. 11 shows an example of a computing device, according to an exemplary embodiment of the invention.

Implementations of the present disclosure may be implemented in and used with a variety of component and network architectures. FIG. 11 is an example of computing device 700, such as a computer, suitable for implementation in exemplary embodiments of the present disclosure. The computing device 700 may include a bus 710, which interconnects major components of the computing device 700, such as a central processor 780; a memory 770 (typically RAM, but which may also include ROM, flash RAM, or the like); an input/output controller 760; a user display 720, such as a display screen via a display adapter; a user input interface 730, which may include one or more controllers and associated user input devices such as a keyboard, mouse, and the like, and may be closely coupled to the I/O controller 760; fixed storage 740, such as a hard drive, flash storage, Fiber Channel network, SAN device, SCSI device, and the like; and a removable media component 750 operative to control and receive an optical disk, flash drive, and the like.

The bus 710 may allow data communication between the central processor 780 and the memory 770, which may include read-only memory (ROM) or flash memory (neither shown), and random-access memory (RAM) (not shown), as previously noted. The RAM may generally be the main memory into which the operating system and application programs are loaded. The ROM or flash memory can contain, among other code, the Basic Input-Output system (BIOS) which controls basic hardware operation such as the interaction with peripheral components. Applications resident with the computing device 700 may generally be stored on and accessed via a computing device readable medium, such as a hard disk drive (e.g., fixed storage 740), an optical drive, floppy disk or other storage medium.

The fixed storage 730 may be integral with the computing device 700 or may be separate and accessed through other interfaces. A network interface 790 may provide a direct connection to a remote server via a telephone link, to the Internet via an internet service provider (ISP), or a direct connection to a remote server via a direct network link to the Internet via a POP (point of presence) or other technique. The network interface 790 may provide such connection using wireless techniques, including digital cellular telephone connection, Cellular Digital Packet Data (CDPD) connection, digital satellite data connection, or the like. For example, the network interface 790 will allow the computing device to communicate with other computing devices via one or more local, wide-area, or other networks, as shown in FIG. 12.

Many other devices or components (not shown) may be connected in a similar manner (e.g., document scanners, digital cameras, and so on). Conversely, all the components shown in FIG. 11 need not be present to practice the present invention. The components can be interconnected in different ways from that shown. The operation of a computing device such as that shown in FIG. 11 is readily known in the art, and is not discussed in detail in this application. Code to implement the present disclosure can be stored in computing device-readable storage media such as one or more of the memories 770, fixed storage 740, removable media 750 or on a remote storage location.

Figure 12:
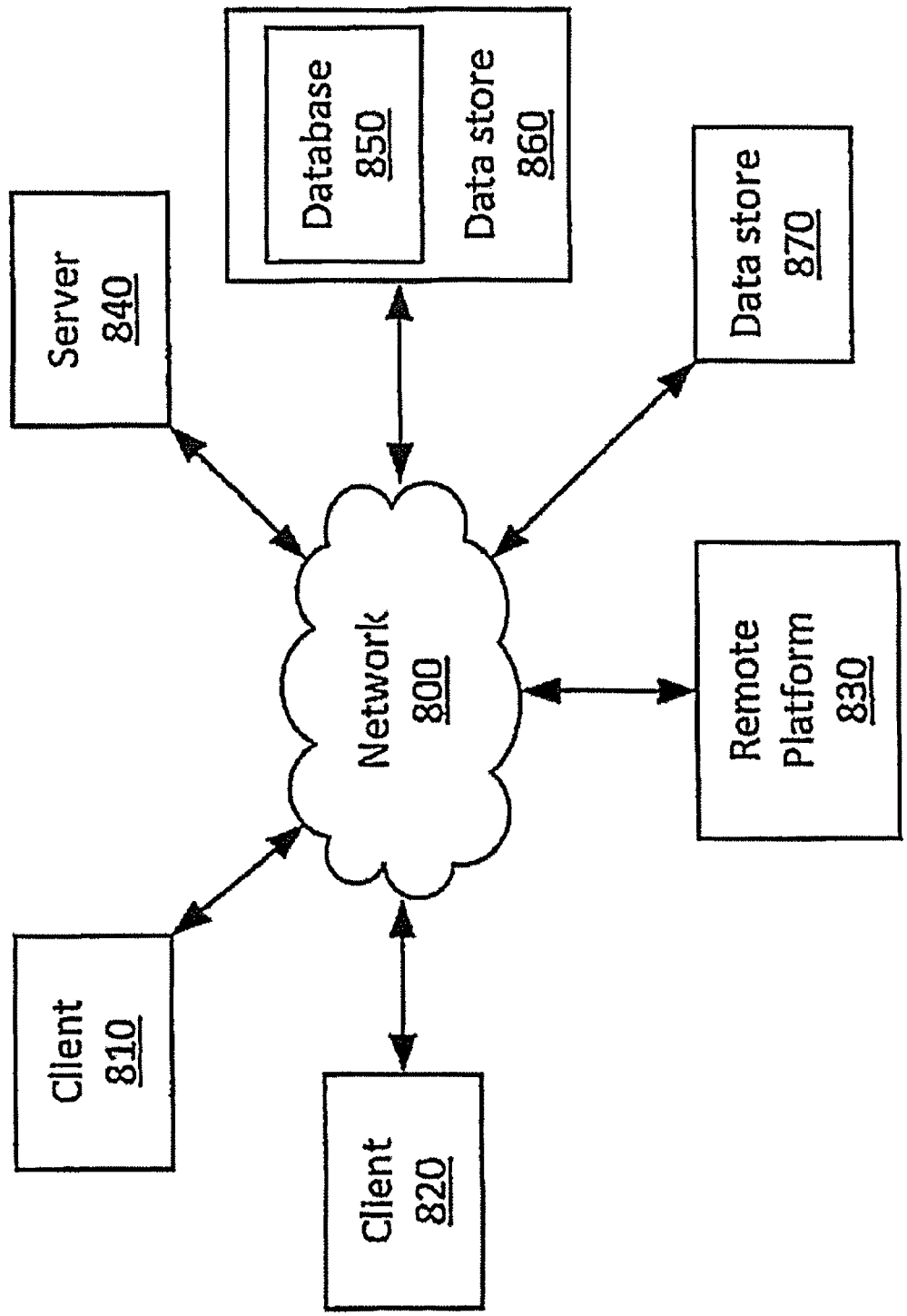
FIG. 12 shows an example of a network arrangement according to an exemplary embodiment of the invention.

FIG. 12 shows an example network arrangement according to an implementation of the disclosure. One or more clients 810, 820, such as local computing devices, smart phones, tablet computing devices, and the like may connect to other devices via one or more networks 800. The network may be a local network, wide-area network, the Internet, or any other suitable communication network or networks, and may be implemented on any suitable platform including wired and/or wireless networks. The clients may communicate with one or more servers 840 and/or databases 850. The devices may be directly accessible by clients 810, 820, or one or more other devices may provide intermediary access, such as where a server 840 provides access to resources stored in a database 850. The clients 810, 820 also may access remote platforms 830 or services provided by remote platforms 830 such as cloud computing arrangements and services. The remote platform 830 may include one or more servers 840 and/or databases 850.

More generally, various implementations of the presently disclosure may include or be implemented in the form of computing device-implemented processes and apparatuses for practicing those processes. Implementations also may be implemented in the form of a computing device program product having computing device program code containing instructions implemented in non-transitory and/or tangible media, such as floppy diskettes, CD-ROMs, hard drives, USB (universal serial bus) drives, flash drives or any other machine readable storage medium, wherein, when the computing device program code is loaded into and executed by a computing device, the computing device becomes an apparatus for practicing implementations of the invention. Implementations also may be implemented in the form of computing device program code, for example, whether stored in a storage medium, loaded into and/or executed by a computing device, or transmitted over some transmission medium, such as over electrical wiring or cabling, through fiber optics, or via electromagnetic radiation; wherein when the computing device program code is loaded into and executed by a computing device, the computing device becomes an apparatus for practicing implementations of the disclosure. When implemented on a general-purpose microprocessor, the computing device program code segments may configure the microprocessor to create specific logic circuits. In some configurations, a set of computing device-readable instructions stored on a computing device-readable storage medium may be implemented by a general-purpose processor, which may transform the general-purpose processor or a device containing the general-purpose processor into a special-purpose device configured to implement or carry out the instructions. Implementations may be implemented using hardware that may include a processor, such as a general-purpose microprocessor and/or an Application Specific Integrated Circuit (ASIC) that implements all or part of the techniques according to implementations of the disclosure in hardware and/or firmware. The processor may be coupled to memory, such as RAM, ROM, flash memory, a hard disk or any other device capable of storing electronic information. The memory may store instructions adapted to be executed by the processor to perform the techniques according to implementations of the invention.

The foregoing description, for purpose of explanation, has been described with reference to specific implementations. However, the illustrative discussions above are not intended to be exhaustive or to limit implementations of the disclosure to the precise forms disclosed. Many modifications and variations are possible in view of the above teachings. The implementations were chosen and described in order to explain the principles of implementations of the invention and their practical applications, to thereby enable others skilled in the art to utilize those implementations as well as various implementations with various modifications as may be suited to the particular use contemplated. The invention is not to be considered to be limited by the exemplary embodiments provided, but by the scope of the appended claims.

The invention claimed is:

1. A method for determining the compatibility of one or more candidates for potential association with a team-of-interest comprised of two or more persons that share in at least one of an interests, objective and task, the method comprising:
   a. developing a stimulus dataset composed of one or more stimuli to elicit one or more of a psychophysiologic response from members of said team-of-interest and one or more of said candidate for association with said team-of-interest to corroborate one or more psychological characteristics of said team-of-interest;
   b. presenting stimuli of said stimulus dataset to each of one or more selected high-performing persons of said team-of-interest by one or more of a sensory presentation device to produce a psychophysiological response for each of said high-performing members of said team-of-interest;
   c. presenting stimuli of said stimulus dataset to each of one or more selected low-performing persons of said team-of-interest by one or more of said sensory presentation devices to produce a psychophysiological response of said low-performing members of said team-of-interest;
   d. training a machine learning algorithm with said psychophysiological response for each of said high-performing members of said team-of-interest and said psychophysiological response for each of said low-performing members of said team-of-interest;
   e. extracting a psychophysiological response signature common to high-performing members of said team-of-interest using said machine learning algorithm;
   f. extracting a psychophysiological response signature common to low-performing persons of said team-of-interest using said machine learning algorithm;
   g. developing a matching algorithm using machine learning techniques to assess the degree of similarity of psychophysiological responses;
   h. presenting stimuli of said stimulus dataset to each of said one or more candidates for potential association with said team-of-interest by one or more of said sensory presentation devices to produce a psychophysiological response for each of said one or more candidates;
   i. computing a compatibility score using said matching algorithm for each of said one or more candidates by comparing said psychophysiological response of said one or more candidates to said psychophysiological response signature common to high-performing persons of said team-of-interest and with said psychophysiological response signature common to low-performing persons of said team-of-interest; and
   j. determining if said compatibility score of said one or more candidates exceeds a selection threshold score correlated with high-performing persons in said team-of-interest.

2. The method of claim 1, wherein a new team of a team-of-interest type is populated by said one or more candidates having compatibility scores exceeding said selection threshold score correlated to high-performing persons of said team-of-interest type.

3. The method of claim 2, wherein team-of-interest types include boyfriend and girlfriend; husband and wife; CEO and COO and CTO, GM and HR and CFO; quarterback and coach; receiver and running back; pilot and gunner; tank crew; or pilot and wingman.

4. The method of claim 1, wherein developing said stimulus dataset includes:
   a. identifying subsets of high- and low-performing individuals of said team-of-interest;
   b. identifying performance and psychological characteristics common to subsets of high- and low-performing individuals of said team-of-interest;
   c. identifying stimuli elements of said stimulus dataset to corroborate the presence or absence of performance and psychological characteristics of team members; and
   d. identifying physical measures of psychophysiological response to stimuli indicative of the presence or absence of performance and psychological characteristics of team members.

5. The method of claim 4, wherein development of said stimulus dataset includes
   modification of stimuli elements of said stimulus dataset until a representative psychophysiological response signature of members of said high-performing subset is distinctly different from the psychophysiological response signature of said low-performing subset with a high probability of detection (Pd) of said high-performing subset in the team-of-interest and low probability of falsely associating members among the said low-performing subset to said high-performing subset.

6. The method of claim 1, further comprising:
dynamically selecting and presenting by a control computer stimulus datasets to candidates at lower levels of abstraction based on how well said candidate's psychophysiological response to said stimulus dataset at high levels of abstraction matches said psychophysiological response signature of high-performing members of said team-of-interest.

7. The method of claim 1, further comprising:
a Brainwave Compatibility technique is employed to identify the best match for the technical and interpersonal contributions of a team member who is departing a team-of-interest; wherein selection of a replacement team member is designed to improve team performance or compatibility among other team members.

8. The method of claim 1 in which presentation of stimuli of said stimulus datasets by said one or more sensor presentation devices is controlled by a control computer.

9. The method of claim 4 in which said low-performing subset of said team-of-interest is populated by selection of individuals from the general population.

* * * * *